United States Patent
Ozawa et al.

(10) Patent No.: US 10,869,598 B2
(45) Date of Patent: Dec. 22, 2020

(54) EYEBALL OPTICAL MEASURING DEVICE AND EYEBALL OPTICAL MEASURING METHOD

(71) Applicant: FUJI XEROX CO., LTD., Tokyo (JP)

(72) Inventors: Hideaki Ozawa, Ebina (JP); Kazuyuki Matsushita, Ebina (JP); Kazutaka Takeda, Ebina (JP); Kouhei Yukawa, Ebina (JP); Taku Kinoshita, Ebina (JP); Hideo Nakayama, Ebina (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 15/723,314

(22) Filed: Oct. 3, 2017

(65) Prior Publication Data

US 2018/0098695 A1 Apr. 12, 2018

(30) Foreign Application Priority Data

Oct. 6, 2016 (JP) .................. 2016-198384

(51) Int. Cl.
*A61B 3/10* (2006.01)
*A61B 3/00* (2006.01)
*A61B 3/117* (2006.01)
*A61B 5/145* (2006.01)
*A61B 5/1455* (2006.01)
*A61B 5/00* (2006.01)
*A61B 3/11* (2006.01)

(52) U.S. Cl.
CPC .......... *A61B 3/117* (2013.01); *A61B 5/1455* (2013.01); *A61B 5/14507* (2013.01); *A61B 5/14532* (2013.01); *A61B 5/6821* (2013.01); *A61B 3/112* (2013.01); *A61B 2562/0233* (2013.01)

(58) Field of Classification Search
CPC .......... A61F 9/008; A61F 2009/00868; A61F 2009/00872; A61F 9/0079; A61B 3/112; A61B 3/117; A61B 5/14507; A61B 5/14532; A61B 5/1455
USPC ........ 351/200, 205, 206, 209–211, 221, 222, 351/223
See application file for complete search history.

(56) References Cited

U.S. PATENT DOCUMENTS 6,166,807 A 12/2000 Kawamura et al.
6,466,320 B1 10/2002 Kawamura et al.
(Continued)

FOREIGN PATENT DOCUMENTS

JP 09-138231 A 5/1997
JP 2002-000570 A 1/2002
(Continued)

OTHER PUBLICATIONS

Translation of Notice of Reasons for Refusal dated Aug. 11, 2020, issued by the Japanese Patent Office in application No. 2016-198384.

*Primary Examiner* — Brandi N Thomas
(74) *Attorney, Agent, or Firm* — Sughrue Mion, PLLC (57) ABSTRACT

An eyeball optical measuring device includes: an optical measuring unit that irradiates an eyeball of a subject with measuring light to perform an optical measurement of the eyeball; and a light irradiation unit that irradiates the eyeball with irradiation light prior to the optical measurement by the optical measuring unit, the irradiation light having a lower energy density than an energy density of the measuring light.

16 Claims, 9 Drawing Sheets

(56) References Cited

U.S. PATENT DOCUMENTS

| | | | | |
|---|---|---|---|---|
| 2001/0056228 A1* | 12/2001 | Utsugi | ............... | A61B 5/0088 600/300 |
| 2003/0016333 A1* | 1/2003 | Ono | ................... | A61B 3/1233 351/221 |
| 2011/0267582 A1* | 11/2011 | Endo | ..................... | A61B 3/112 351/206 |
| 2014/0211156 A1* | 7/2014 | Masaki | ................ | A61B 3/102 351/206 |

FOREIGN PATENT DOCUMENTS

| | | | | |
|---|---|---|---|---|
| JP | 2002-238852 A | | 8/2002 | |
| JP | 2003-010127 A | | 1/2003 | |
| KR | 10-2012-0054474 | * | 5/2012 | .......... A61B 5/0066 |

* cited by examiner

EYEBALL OPTICAL MEASURING DEVICE AND EYEBALL OPTICAL MEASURING METHOD

CROSS REFERENCE TO RELATED APPLICATIONS

This application is based on and claims priority under 35 USC § 119 from Japanese Patent Application No. 2016-198384 filed Oct. 6, 2016.

BACKGROUND

Technical Field

The present invention relates to an eyeball optical measuring device and an eyeball optical measuring method.

Related Art

Conventionally, an eyeball measurement positioning device has been known that positions a light path based on reflected light from an eyeball in order to measure a glucose concentration in the aqueous humor based on the amount of absorption of light passing through the eyeball or based on a polarization plane rotation angle of the light passing through the eyeball. The measured glucose concentration in the aqueous humor is used to estimate a glucose concentration in blood.

SUMMARY

According to an aspect of the present invention, there is provided an eyeball optical measuring device including: an optical measuring unit that irradiates an eyeball of a subject with measuring light to perform an optical measurement of the eyeball; and a light irradiation unit that irradiates the eyeball with irradiation light prior to the optical measurement by the optical measuring unit, the irradiation light having a lower energy density than an energy density of the measuring light.

BRIEF DESCRIPTION OF THE DRAWINGS

An exemplary embodiment of the present invention will be described in detail based on the following figures, wherein:

FIGS. 4A and 4B illustrate relationship between the pupil diameter and the luminance based on the formula (1), wherein FIG. 4A shows the luminance in a logarithmic scale, and FIG. 4B shows the luminance in a linear scale;

DETAILED DESCRIPTION

Hereinafter, the exemplary embodiments will be described in detail with reference to attached drawings.

In the following description, optical measurement of an eyeball is referred to as the "optical measurement", and a device for optical measurement of an eyeball is referred to as the "optical measuring device".

First Exemplary Embodiment (Optical Measuring Device 1)

Figure 1:
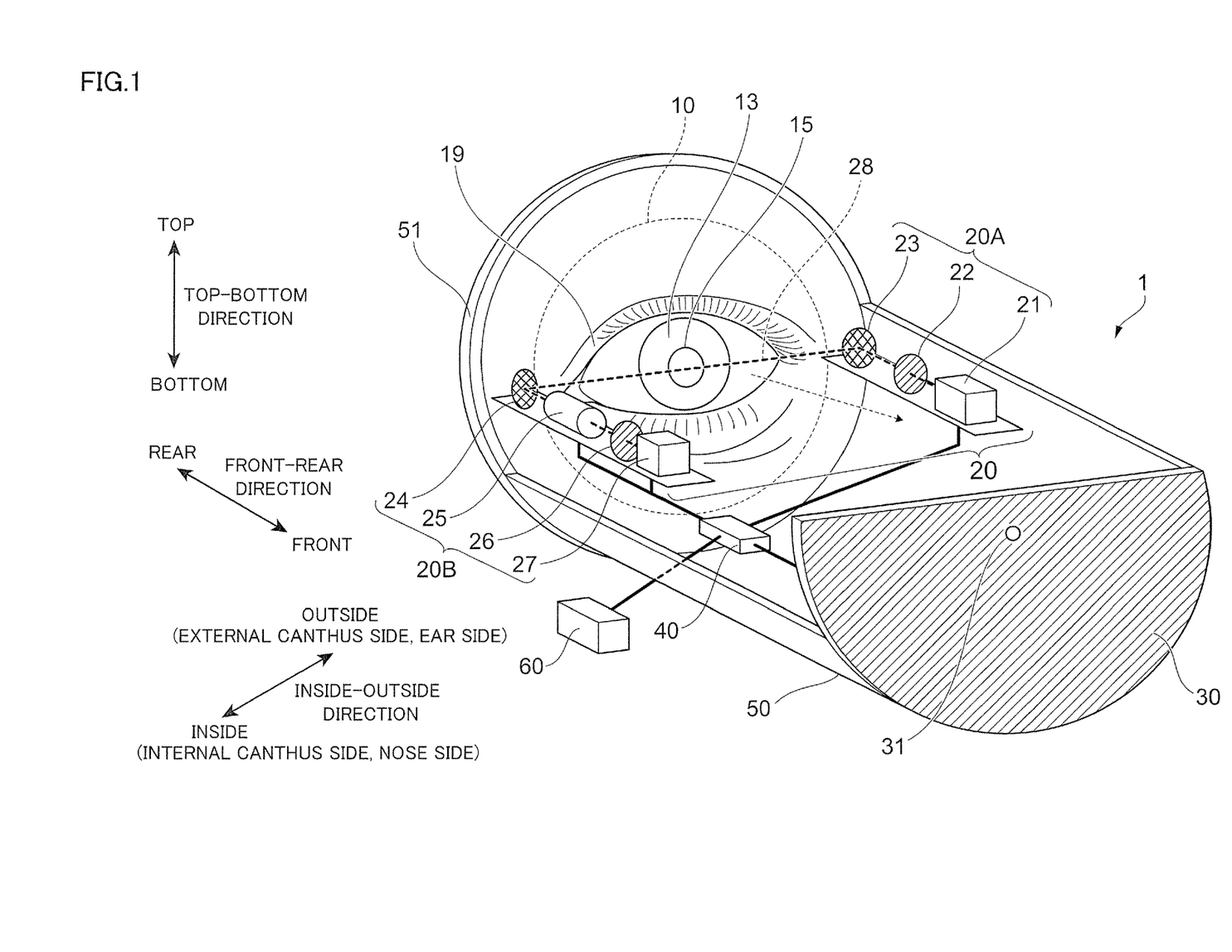
FIG. 1 illustrates an exemplary configuration of an optical measuring device according to the first exemplary embodiment.

FIG. 1 illustrates an exemplary configuration of an optical measuring device 1 according to the first exemplary embodiment.

The optical measuring device 1 includes an optical system 20, a light irradiation unit 30, a controller 40, a holding unit 50, and a calculation unit 60. The optical system 20 is used for the optical measurement of a characteristic of the aqueous humor in an anterior chamber 13 of an eyeball 10 of a subject. The light irradiation unit 30 irradiates the eyeball 10 with light. The controller 40 controls the optical system 20 and the light irradiation unit 30. The holding unit 50 holds the optical system 20 and the controller 40. The calculation unit 60 calculates a characteristic of the aqueous humor on the basis of data on the optical measurement by the optical system 20.

The eyeball 10 shown in FIG. 1 is of the left eye.

The optical system 20 is a specific example of the optical measuring unit.

In the following description, in the optical measuring device 1 shown in FIG. 1, a direction connecting the top side and the bottom side of the paper surface may be referred to as the top-bottom direction. A direction connecting the front side and the rear side of the subject may be referred to as the front-rear direction. A direction connecting the inside (internal canthus side, or nose side) and the outside (external canthus side, or ear side) of the subject may be referred to as the inside-outside direction.

The characteristic of the aqueous humor to be measured by the optical measuring device 1 is, for example, an angle of rotation of the polarization plane of linearly polarized light (an optical rotation angle $\alpha_M$) produced by optically active substances contained in the aqueous humor, or a degree of color absorption for circularly polarized light (circular dichroism). In the present specification, the term "polarization plane" refers to a plane on which the electric field of linearly polarized light oscillates.

Figure 3:
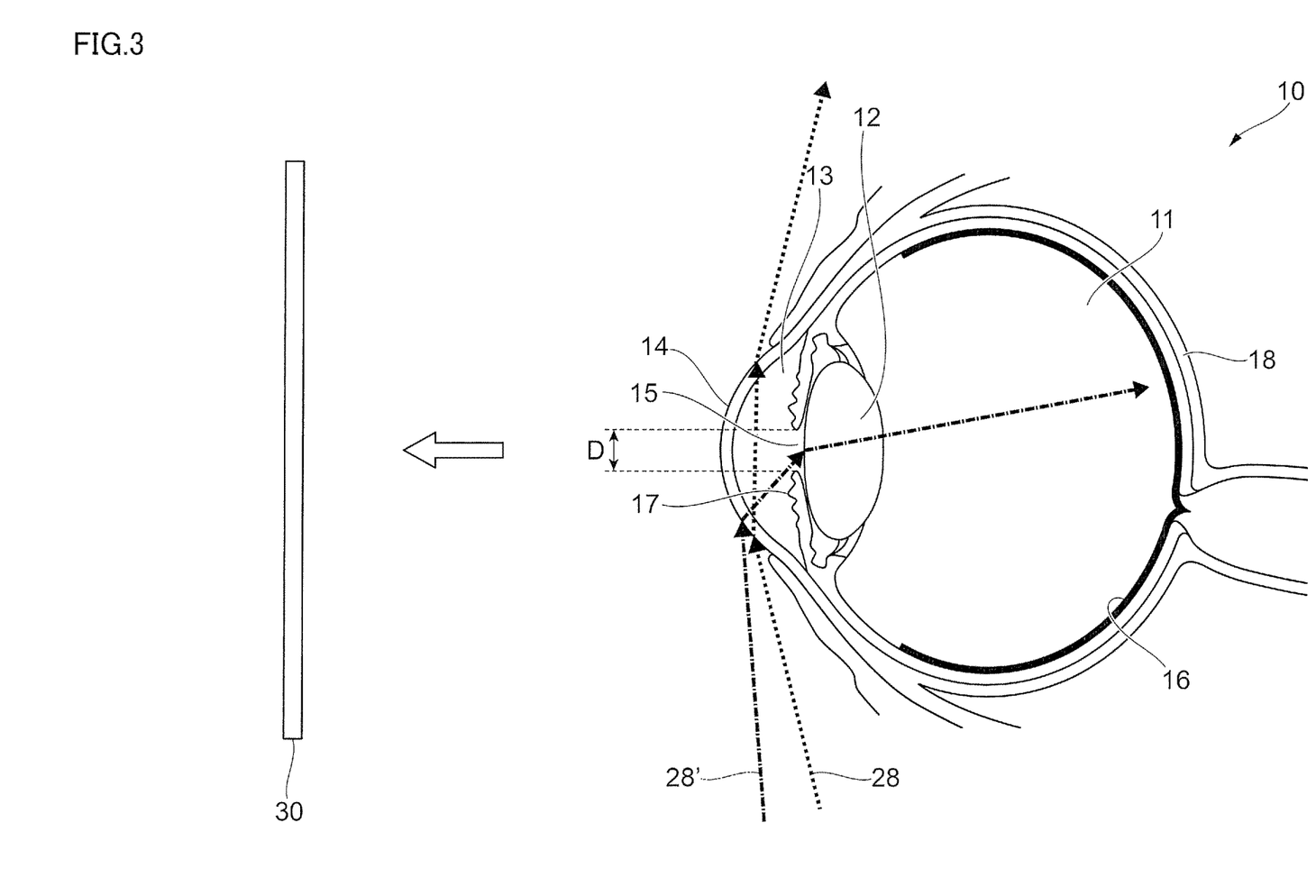
FIG. 3 is a schematic view of an eyeball.

The anterior chamber 13 of the eyeball 10 is a region between a crystalline lens 12 (see FIG. 3 described later), which serves as a lens, and a cornea 14 (see FIG. 3). The anterior chamber 13 is filled with the aqueous humor. The anterior chamber 13 is circular when viewed from the front. Although the eyeball 10 is almost spherical, the anterior chamber 13 somewhat projects from the sphere surface. FIG. 1 shows a state where an eyelid 19 is open.

The optical system 20 includes a light emitting unit 21, a polarizer 22, a first mirror 23, a second mirror 24, a compensator 25, an analyzer 26, and a light receiving unit 27.

The light emitting unit 21 is a light source that emits light used for the optical measurement of the characteristic of the aqueous humor in the anterior chamber 13 of the eyeball 10. The light emitting unit 21 may be either a light source having a wide wavelength range such as a light-emitting diode (LED) or a lamp, or a light source having a narrow wavelength range such as a laser. Employment of a light source having a narrow wavelength range is preferable.

The light emitting unit 21 may be one that emits light of at least two wavelengths.

As described later, light emitted from the light emitting unit 21 to the eyeball 10 of the subject is referred to as the measuring light. In the following description, energy density of the measuring light refers to energy density of the measuring light that has reached a retina 16 of the eyeball 10. If the light emitting unit 21 employs a laser as its light source, the energy density of the measuring light becomes significantly higher than other light sources such as an LED.

The polarizer 22, which is a Nicol prism for example, transmits linearly polarized light having a predetermined polarization plane that is a component of incident light.

The first mirror 23 and the second mirror 24 bend an optical path 28. The first mirror 23 and the second mirror 24 are preferably those that keep the polarization state of linearly polarized light before and after reflection. It is not preferable to use mirrors that disorder the polarization state, such as those that rotate the polarization plane or convert linearly polarized light into elliptically polarized light. When it is not necessary to bend the optical path 28, the first mirror 23 and/or the second mirror 24 may be omitted.

The compensator 25, which is a magneto-optical element such as a Faraday device using a garnet or the like, rotates the polarization plane of linearly polarized light by a magnetic field.

The analyzer 26, which is a member similar to the polarizer 22, transmits linearly polarized light having a predetermined polarization plane.

The light receiving unit 27, which is composed of a light receiving element such as a silicon diode, outputs an output signal corresponding to light intensity.

The light irradiation unit 30 irradiates the eyeball 10 of the subject with light that is different from the measuring light. The light irradiation unit 30 may be either a planar light source or a point light source. In the case of using a planar light source, the light irradiation unit 30 may be a luminescent screen composed of a liquid crystal display (LCD) or the like. In this case, the light irradiation unit 30 may display a mark (target) 31 visually recognizable by the subject to guide the direction (line of sight) of the eyeball 10. In the case of using a luminescent screen, the light irradiation unit 30 may display the characteristic of the aqueous humor (e.g. a concentration of an optically active substance) calculated by the calculation unit 60 after completion of the optical measurement. The following explanation is given using a case where the light irradiation unit 30 is a luminescent screen composed of an LCD.

In the case of using a point light source, the light irradiation unit 30 may be an LED or a lamp. In this case, the mark 31 shown in FIG. 1 may be replaced with such an LED or a lamp.

In the following description, light emitted by the light irradiation unit 30 to the eyeball 10 of the subject is referred to as the irradiation light. Also, energy density of the irradiation light refers to energy density of the irradiation light that has reached the retina 16 of the eyeball 10. The light irradiation unit 30 and the irradiation light will be described in detail later.

Here, the energy density of the measuring light is assumed to be higher than the energy density of the irradiation light.

The controller 40 controls the components of the optical system 20, such as the light emitting unit 21, the compensator 25 and the light receiving unit 27, to obtain optical measurement data on the characteristic of the aqueous humor. The controller 40 also controls the light irradiation unit 30. Further, the controller 40 sends the optical measurement data to the calculation unit 60.

The holding unit 50 holds the optical system 20, the light irradiation unit 30 and the control unit 40. The holding unit 50 holds the optical system 20 so that the optical path 28 set in the optical system 20 goes through the aqueous humor in the anterior chamber 13 in a state where end portions of the holding unit 50 are positioned in contact with predetermined portions around the eyeball 10. To bring the holding unit 50 into contact with the portions around the eyeball 10, the subject or another person may grip the optical measuring device 1 to make the holding unit 50 contact by his/her own hands; alternatively, a driving device may be used to automatically move the optical measuring device 1 in the front-rear direction. The portions with which the holding unit 50 is brought into contact need not necessarily be those around the eyeball 10 as long as the holding unit 50 can be positioned with respect to the eyeball 10, and may be other portions of the face of the subject. Further, the holding unit 50 need not be brought into contact with the face if the holding unit 50 can be positioned without coming into contact with the face.

The optical path 28, which is indicated by a broken line in the figure, is set so that light emitted from the light emitting unit 21 passes across (traverses) the anterior chamber 13 and is received by the light receiving unit 27.

The phrase "pass across (traverse) the anterior chamber 13" means that, when the eyeball 10 is seen from the front, light passes through the anterior chamber 13 in a direction that is closer to the inside-outside direction than the top-bottom direction (i.e. in a direction that forms an angle smaller than +/−45 degrees with the horizontal axis in the inside/outside direction); the phrase includes a case where light passes through the anterior chamber 13 obliquely in the front-rear direction.

The holding unit 50 may include an eyepiece member 51 that fixes the optical measuring device 1 with respect to the eyeball 10 and thereby prevents deviation of the optical path 28.

The holding unit 50 shown in FIG. 1 has a shape obtained by cutting a cylinder with a plane parallel to its axial direction. However, this is to make the optical system 20 visible; the holding unit 50 may be cylindrical. Alternatively, the holding unit 50 may have a tubular shape with an elliptical or rectangular cross section. Further, the holding unit 50 may have a partially cutaway tubular shape like the one shown in FIG. 1.

The holding unit 50 may be an eyeglass frame. That is, the optical measuring device 1 may be a glasses-type device in which the optical system 20, the light irradiation unit 30 and the controller 40 are mounted on glasses.

The calculation unit 60 receives optical measurement data from the controller 40 and calculates the characteristic of the aqueous humor.

Here, the measuring light emitted from the light emitting unit 21 travels along the optical path 28 and enters the light receiving unit 27. More specifically, the measuring light emitted from the light emitting unit 21 toward the eyeball 10 side passes through the polarizer 22 and is then bent by the first mirror 23 in a direction traversing the anterior chamber 13 (i.e. a direction parallel to the eye). Thus the measuring light passes across the anterior chamber 13. After that, the measuring light is bent by the second mirror 24 in a direction away from the eye. Finally, the measuring light passes through the compensator 25 and the analyzer 26 to enter the light receiving unit 27.

In FIG. 1, a part including the light emitting unit 21, the polarizer 22, and the first mirror 23 is a light emitting system 20A. A part including the second mirror 24, the compensator 25, the analyzer 26, and the light receiving unit 27 is a light receiving system 20B.

Note that the positions of the light emitting system 20A and the light receiving system 20B may be interchanged.

Now, a description will be given of an example use of the optical measuring device 1 in which the aqueous humor in the anterior chamber 13 is subjected to the optical measurement and a glucose concentration is calculated.

Amount of insulin to be administered to a diabetic patient is controlled according to the glucose concentration in blood. Accordingly, the diabetic patient is required to recognize the glucose concentration in blood at all times. A major method for measuring the glucose concentration in blood is to stick a fingertip or other sites with an injection needle to acquire a very small amount of blood. However, taking even a very small amount of blood causes the patient to have a pain. Thus, a growing need exits for noninvasive test methods to replace invasive test methods such as one that involves needle sticking.

The aqueous humor in the anterior chamber 13, which has almost the same components as serum, contains proteins, glucose, ascorbic acid, etc. It is known that a correlation exists between the glucose concentration in blood and that in the aqueous humor. The aqueous humor contains no cellular substances that are found in blood, and is little susceptible to light scattering. Further, proteins, proteins, glucose, ascorbic acid, etc. contained in the aqueous humor are optically active substances and have optical rotatory power. Accordingly, the aqueous humor is an effective target for the optical measurement to measure a concentration of, for example, glucose utilizing optical rotatory power.

In methods for optically obtaining a concentration or other characteristics of an optically active substance contained in the aqueous humor, the following two optical paths can be set.

One of the optical paths is an optical path for emitting light to the eyeball 10 substantially perpendicularly, causing reflection of the light at the interface between the cornea 14 (see FIG. 3) and the aqueous humor or the interface between the aqueous humor and the crystalline lens 12 (see FIG. 3), and receiving (detecting) the reflected light. The other of the optical paths is an optical path for emitting light to the eyeball 10 at an angle that makes the light substantially in parallel to the eyeball 10, and receiving (detecting) light that has passed through the aqueous humor in the anterior chamber 13.

Among the above optical paths, employing the optical path for emitting light to the eyeball 10 substantially perpendicularly leads to a higher possibility that the light reaches the retina 16 (see FIG. 3), than employing the optical path for emitting light so as to make the light pass across the anterior chamber 13, which will be described later. In particular, if the light emitting unit 21 employs laser light, which has a high coherence, there is a possibility that the high-energy density light may reach the retina 16 and, depending on the irradiation time, cause a harmful effect on the retina 16.

In contrast, in the case of the optical path for emitting light to the eyeball 10 at an angle that makes the light substantially in parallel to the eyeball 10, light passes across the anterior chamber 13 through the cornea 14 and is then received (detected) as having passed through the aqueous humor. Accordingly, employing this optical path reduces the possibility that the high-energy density light reaches the retina 16. However, even employing this optical path may possibly cause light to reach the retina 16 during adjustment to the optical system 20, due to biological vibrations accompanying breathing or pulsation, or due to change in the state of the cornea 14. For this reason, the present exemplary embodiment reduces the amount of the measuring light that reaches the retina 16.

Here, there is only a limited space to place the light emitting unit 21, the polarizer 22, the compensator 25, the analyzer 26, the light receiving unit 27, etc. of the optical system 20 because the eyeball 10 has an almost spherical outward shape and the nose (nasal bridge) exists on the light emission side or the light reception side.

In view of this, to effectively use the space, the present exemplary embodiment arranges the first mirror 23 and the second mirror 24 to bend the optical path 28 as shown in FIG. 1. This arrangement allows to set the optical path 28 so that light is emitted at an angle that makes the light substantially in parallel to the eyeball 10 and passes across the anterior chamber 13.

It should be noted that the optical path 28 may be bent only at the nose side, without being bent at the ear side. In this case, either the first mirror 23 or the second mirror 24 may be omitted.

Further, if the optical system 20 is small, it is not necessary to bend the optical path 28.

Figure 2:
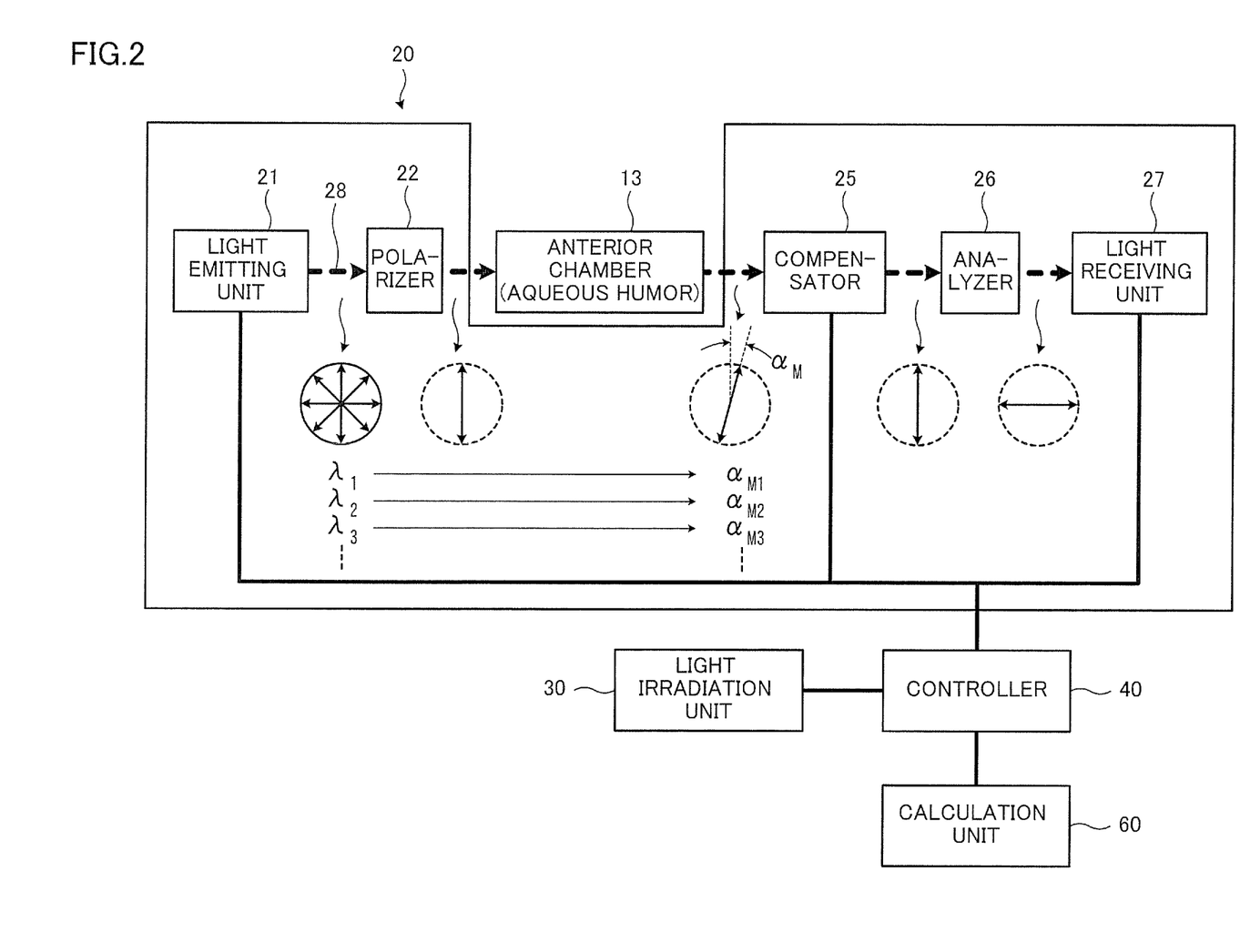
FIG. 2 illustrates a method for measuring an angle of rotation (optical rotation) of the polarization plane produced by optically active substances contained in the aqueous humor in the anterior chamber by means of the optical measuring device.

FIG. 2 illustrates a method for measuring an angle of rotation (optical rotation) of the polarization plane produced by optically active substances contained in the aqueous humor in the anterior chamber 13 by means of the optical measuring device 1. To simplify the explanation, the first mirror 23 and the second mirror 24 are omitted in FIG. 2 assuming that the optical path 28 is not bent (i.e. it is straight).

In the optical system 20 shown in FIG. 2, polarization as viewed from the emission side of light is indicated by an arrow(s) in a circle between adjacent two of the light emitting unit 21, the polarizer 22, the anterior chamber 13, the compensator 25, the analyzer 26, and the light receiving unit 27.

It is assumed that the light emitting unit 21 emits light having random polarization planes. Receiving that light, the polarizer 22 allows passage of linearly polarized light having a predetermined polarization plane. In the specific example shown in FIG. 2, linearly polarized light whose polarization plane is parallel to the paper surface passes through the polarizer 22.

After passing through the polarizer 22, the linearly polarized light undergoes polarization plane rotation by optically active substances contained in the aqueous humor in the anterior chamber 13. In FIG. 2, the polarization plane is rotated by an angle $\alpha_M$ (optical rotation angle $\alpha_M$).

Then, a magnetic field is applied to the compensator 25, whereby the polarization plane that has been rotated by the optically active substances contained in the aqueous humor in the anterior chamber 13 is returned to the original state.

The linearly polarized light that has passed through the analyzer 26 is received by the light receiving unit 27, which then converts the light into an output signal corresponding to the intensity of the light.

An example method for measuring an optical rotation angle $\alpha_M$ using the optical system 20 will be described below.

First, the compensator 25 and the analyzer 26 are set so as to minimize the output signal of the light receiving unit 27 in a state where light emitted from the light emitting unit 21 does not pass through the anterior chamber 13, in the optical system 20 including the light emitting unit 21, the polarizer 22, the compensator 25, the analyzer 26, and the light receiving unit 27. As shown in FIG. 2, in a state where light does not pass through the anterior chamber 13, the polarization plane of the linearly polarized light that has passed through the polarizer 22 is perpendicular to that of the linearly polarized light that passes through the analyzer 26.

In FIG. 2, the polarization plane of the polarizer 22 and the polarization plane of the linearly polarized light before passing through the analyzer 26 are both parallel to the paper surface. However, in a case where the polarization plane is rotated by the compensator 25 in advance, the polarization plane of the linearly polarized light before passing through the analyzer 26 may be inclined from the plane that is parallel to the paper surface. That is, the compensator 25 and the analyzer 26 are set so as to minimize the output signal of the light receiving unit 27 in a state where light emitted from the light emitting unit 21 does not pass through the aqueous humor in the anterior chamber 13.

Then, light is caused to pass through the anterior chamber 13. This causes the polarization plane to be rotated by the optically active substances contained in the aqueous humor in the anterior chamber 13. As a result, the output signal of the light receiving unit 27 deviates from the minimum value. In consideration of this, the magnetic field to be applied to the compensator 25 is set so as to minimize the output signal of the light receiving unit 27. That is, the polarization plane is rotated by the compensator 25 so as to be perpendicular to the polarization plane for passage through the analyzer 26.

At this time, the polarization plane rotation angle caused by the compensator 25 corresponds to an optical rotation angle $\alpha_M$ produced by the optically active substances contained in the aqueous humor. Since the relationship between the magnitude of the magnetic field applied to the compensator 25 and the polarization plane rotation angle is known in advance, an optical rotation angle $\alpha_M$ can be obtained from the magnitude of the magnetic field applied to the compensator 25.

Although the above example uses the compensator 25 to measure an optical rotation angle $\alpha_M$, other devices than the compensator 25 may be used to measure an optical rotation angle $\alpha_M$. Additionally, although FIGS. 1 and 2 show the crossed Nicols method (with the use of the compensator 25), which is the most fundamental method for measuring a polarization plane rotation angle (optical rotation angle $\alpha_M$), other measuring methods such as the rotating analyzer method, Faraday modulation method, and optical delay modulation method may be used.

A more specific description for measuring an optical rotation angle $\alpha_M$ is given below. Light beams having different wavelengths $\lambda$ ($\lambda_1$, $\lambda_2$, $\lambda_3$, ... ) are emitted from the light emitting unit 21 to the aqueous humor in the anterior chamber 13, and optical rotation angles $\alpha_M$ ($\alpha_{M1}$, $\alpha_{M2}$, $\alpha_{M3}$, ... ) are measured for respective light beams. Each set of a wavelength $\lambda$ and an optical rotation angle $\alpha_M$ is fed to the calculation unit 60, which then calculates a concentration of a target optically active substance.

As mentioned above, the aqueous humor contains multiple optically active substances. Accordingly, each measured optical rotation angle $\alpha_M$ is the sum of optical rotation angles $\alpha$ of the multiple optically active substances. It is thus necessary to calculate a concentration of the target optically active substance from the measured optical rotation angle $\alpha_M$. Such calculation of a concentration of the target optically active can be made by any known method such as one disclosed in, for example, Japanese Patent Application Laid-Open Publication No. H09-138231, and thus description thereof is omitted.

FIG. 3 is a schematic view of the eyeball 10.

As shown in FIG. 3, the eyeball 10 has an almost spherical outward shape and has a vitreous body 11 at its center. The crystalline lens 12, which serves as a lens, is buried in a part of the vitreous body 11. The anterior chamber 13 is located outside the crystalline lens 12 and the cornea 14 is located outside the anterior chamber 13.

The crystalline lens 12 is surrounded by an iris 17. A pupil 15 is at the center of the iris 17. The vitreous body 11 is covered with the retina 16 except a portion that is in contact with the crystalline lens 12. A sclera 18 is located outside the retina 16. In other words, the outer portion of the eyeball 10 is covered with the cornea 14 and the sclera 18.

The anterior chamber 13 is the region that is surrounded by the cornea 14 and the crystalline lens 12, and convexly projects from the sphere of the eyeball 10. The anterior chamber 13 is filled with the aqueous humor.

The optical path 28 will now be explained. FIG. 3 shows the optical path 28 indicated by a broken line and an optical path 28' indicated by a long and short dashed line.

As explained with reference to FIG. 1, light along the optical path 28 is incident at an angle that makes the light substantially in parallel to the eyeball 10, and passes across the anterior chamber 13 through the cornea 14.

In contrast, light along the optical path 28' enters the anterior chamber 13 through the cornea 14 and then enters the crystalline lens 12, finally reaching the retina 16. As explained above, if light with a high energy density reaches the retina 16, such light may cause a harmful effect on the retina 16, depending on the irradiation time.

Light may deviate from the original optical path 28 to the optical path 28', during adjustment to the optical system 20 to establish the original optical path 28, or due to biological vibrations or change in the state of the cornea 14.

In view of this, the present exemplary embodiment reduces the energy of the light that reaches the retina 16, even if the light deviates from the optical path 28.

It is known that a diameter D of the pupil 15 of the eyeball 10 (hereinafter referred to as the pupil diameter D) is expressed by the following formula (1), which uses luminance L of the light irradiation unit 30, such as a screen arranged in front of the eyeball 10.

[Formula 1]

$$D = 4.90 - 3.0 \times \tan h(0.40 \times \log(L)) \quad (1)$$

Figure 4A:
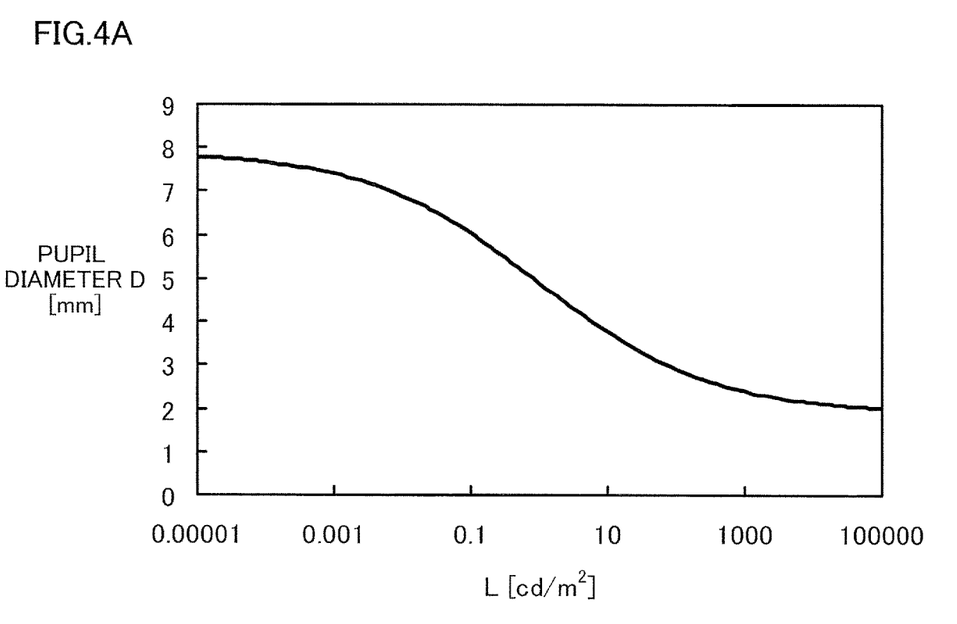
Figure 4B:
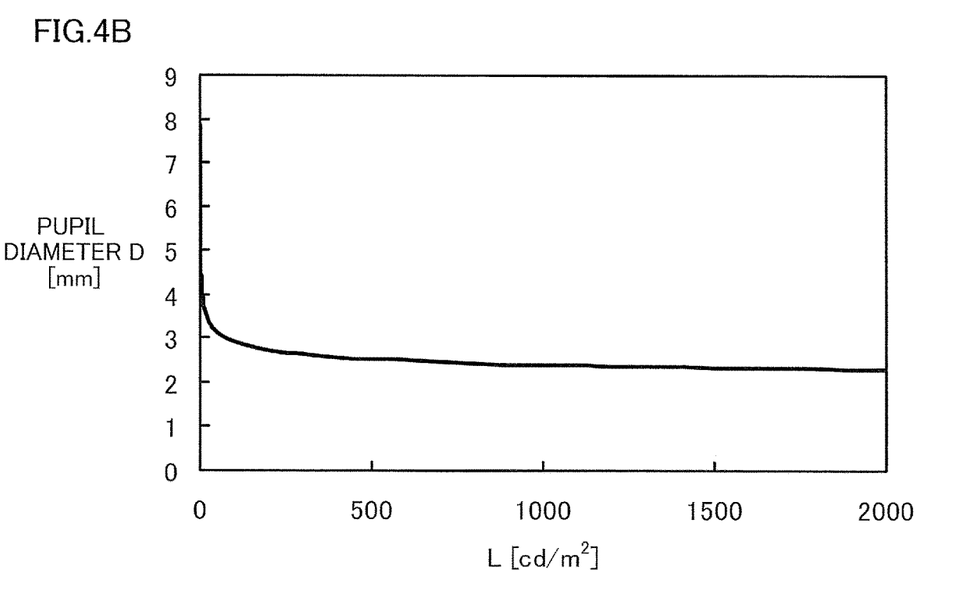

FIGS. 4A and 4B illustrate relationship between the pupil diameter D and the luminance L based on the formula (1). FIG. 4A shows the luminance L in a logarithmic scale. FIG. 4B shows the luminance L in a linear scale.

As can be seen from FIGS. 4A and 4B, the pupil diameter D decreases as the luminance L increases. At the luminance L of 500 cd/m$^2$ or more, the pupil diameter D becomes less than 2.5 mm and shows less change in the diameter.

As the pupil diameter D gets smaller, the measuring light with a high energy density and incident on the eyeball 10 is more likely to be blocked by the iris 17 (see FIG. 3). The amount of the measuring light that reaches the retina 16 can be thus reduced, as compared with a case where the pupil diameter D is not small.

Note that the luminance of 500 cd/m$^2$ is comparable to the luminance of lighting of a store, causing no harmful effect on the retina 16.

Thus, in the first exemplary embodiment, the light irradiation unit 30 is arranged in front of the eyeball 10 of the subject to irradiate the eyeball 10 with the irradiation light prior to the optical measurement by the optical system 20. This makes the pupil diameter D smaller than the diameter before irradiation by the light irradiation unit 30. With this smaller pupil diameter D, the optical system 20 performs the optical measurement. This allows to reduce the amount of the high-energy density measuring light that reaches the retina 16.

In the case where the light irradiation unit 30 is a planar light source, the entire plane of the light irradiation unit 30 may be set to have a predetermined luminance L.

In the case where the light irradiation unit 30 is a display such as an LCD, the light irradiation unit 30 may display the mark (target) 31 as shown in FIG. 1. The mark 31 may be set to have a predetermined luminance L while the surrounding area of the mark 31 may be set to have a luminance lower than the predetermined luminance L. This setting makes the mark 31 a bright spot that is brighter than the surrounding area of the mark 31. Alternatively, the surrounding area of the mark 31 may be set to have a predetermined luminance L while the mark 31 may be set to have a luminance lower than the predetermined luminance L. This setting makes the mark 31 a dark spot that is darker than the surrounding area of the mark 31. The mark 31 as a dark spot is less dazzling than as being a bright spot, and can reduce the possibility that the subject turns his/her eye away from the mark 31. In other words, the mark 31 as a dark spot can more easily lead the eyeball 10 of the subject to a state suitable for the optical measurement.

In the case where the light irradiation unit 30 is a spot light source, the spot light may be set to have a predetermined luminance L.

That is, the light irradiation unit 30 may be configured to emit light to the eyeball 10 of the subject in such a manner as to make the pupil diameter D of the eyeball 10 small at the time of the optical measurement.

(Method for Optical Measurement of the Eyeball)

Figure 5:
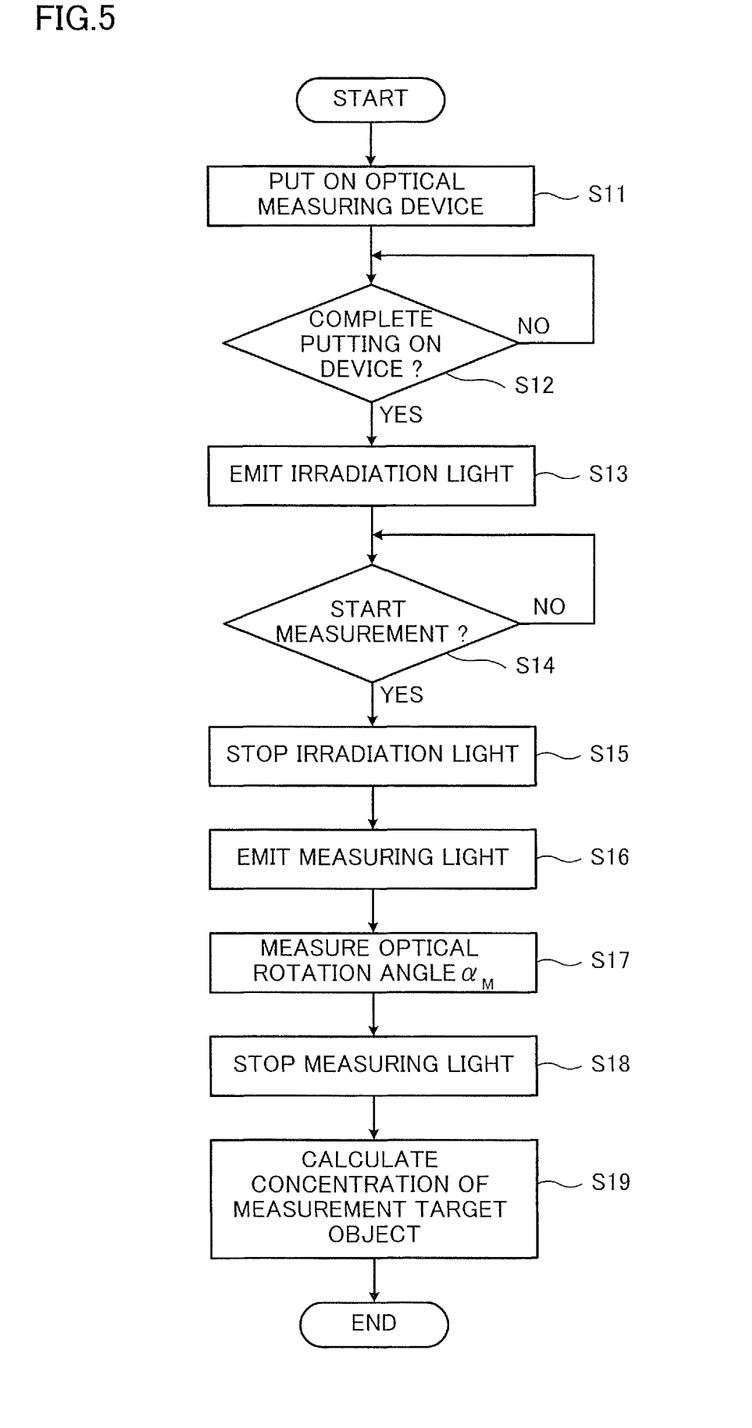
FIG. 5 is a flowchart for explaining the optical measuring method for measuring a concentration of an optically active substance contained in the aqueous humor in the anterior chamber by means of the optical measuring device according to the first exemplary embodiment.

FIG. 5 is a flowchart for explaining the optical measuring method for measuring a concentration of an optically active substance contained in the aqueous humor in the anterior chamber 13 by means of the optical measuring device 1 according to the first exemplary embodiment.

The explanation is given using an example where the light irradiation unit 30 is a planar light source such as a display (e.g. an LCD) and displays the mark 31 as a bright spot.

First, the subject turns on the optical measuring device 1 and puts on the device 1 (step 11, denoted by S11 in FIG. 5; similar abbreviations will be made in the subsequent steps in the figure). With the optical measuring device 1 turned on, the optical system 20, the light irradiation unit 30, the controller 40, and the calculation unit 60 become operational. At this time, the light emitting unit 21 of the optical system 20 does not emit the measuring light.

Then, the controller 40 determines whether the subject has completed putting on the optical measuring device 1 (step 12). For example, the optical measuring device 1 is fitted with a notification button that is pressed by the subject to notify that he/she has completed putting on the optical measuring device 1. The controller 40 determines whether the subject has completed putting on the optical measuring device 1 on the basis of whether the notification button has been pressed or not.

If the determination at step 12 is negative (NO), that is, if the subject has not completed putting on the optical measuring device 1, the process returns to step 12 to wait for completion.

If the determination at step 12 is positive (YES), that is, if the subject has completed putting on the optical measuring device 1, the controller 40 controls the light irradiation unit 30 to emit the irradiation light to the eyeball 10 (step 13). At this time, the light irradiation unit 30 displays the mark (target) 31.

Then, the controller 40 determines whether to start an optical measurement (step 14). For example, the optical measuring device 1 is fitted with a command button that is pressed by the subject to command the start of an optical measurement at a timing when he/she recognizes the mark (target) 31 and directs his/her eye to the mark (target) 31. The controller 40 determines whether to start an optical measurement on the basis of whether the command button has been pressed or not.

If the determination at step 14 is negative (NO), that is, if an optical measurement should not be started, the process returns to step 14 to wait for the command to start the measurement.

If the determination at step 14 is positive (YES), that is, if an optical measurement has been commanded, the controller 40 stops the light irradiation unit 30 from emitting the irradiation light (step 15).

Then, the controller 40 controls the light emitting unit 21 to emit the measuring light (step 16). The controller 40 then adjusts the optical system 20 to establish the optical path 28 that passes through the anterior chamber 13, and measures an optical rotation angle $\alpha_M$ on the basis of the measuring light that has passed through the aqueous humor in the anterior chamber 13 (step 17). Upon completion of the measurement, the controller 40 stops the light emitting unit 21 from emitting the measuring light (step 18).

Then, the controller 40 sends optical measurement data, such as the measured optical rotation angle $\alpha_M$, to the calculation unit 60.

In response, the calculation unit 60 calculates a concentration of a target optically active substance (measurement target object) contained in the aqueous humor (step 19).

The controller 40 may then receive the data on the concentration of the measurement target object calculated by the calculation unit 60 and display the concentration on the light irradiation unit 30.

In the flowchart of FIG. 5, if the optical measurement is commanded at step 14, the light irradiation unit 30 is stopped from emitting the irradiation light. This is because if the irradiation light enters the light receiving portion 27 of the optical system 20 and is superimposed on (mixed in) the measuring light, an error may occur in the measurement value. In other words, in order to prevent the irradiation light from being superimposed on (mixed in) the measuring light, emission of the irradiation light is stopped prior to the start of the measurement.

However, after the stop of irradiation of the eyeball 10 with the irradiation light from the light irradiation unit 30, the pupil 15, which has been narrowed (made smaller) by the irradiation light, gradually widens. For this reason, it is desirable to measure the optical rotation angle $\alpha_M$ at step 17 during the period when the pupil 15 is being narrowed. To put it the other way around, emission of the irradiation light from the light irradiation unit 30 is preferably made at a timing that is prior to the measurement of the optical rotation angle $\alpha_M$ at step 17 and that ensures that the pupil 15 of the eyeball 10 narrowed by the irradiation light does not return to its pre-irradiation size during the optical measurement.

Note that, once the optical system 20 has been adjusted to establish the optical path 28 passing through the anterior chamber 13, the measuring light is less likely to reach the retina 16 even with the widened pupil 15 (i.e. even if the pupil 15 is larger than when it is being irradiated with the irradiation light). However, due to biological vibrations or change in the state of the cornea 14, the measuring light may still reach the retina 16 through the widened pupil 15. Thus, the pupil 15 is desirably kept narrowed.

Second Exemplary Embodiment

As shown in step 15 of the flowchart in FIG. 5, the first exemplary embodiment stops emission of the irradiation light at the time of the optical measurement. In this case, the pupil 15, which has been narrowed, gradually widens after the stop of the emission.

The second exemplary embodiment differentiates the wavelength of the irradiation light emitted by the light irradiation unit 30 from the wavelength of the measuring light emitted by the light emitting unit 21 of the optical system 20, so that the irradiation light continues to be emitted during emission of the measuring light. This allows the eyeball 10 to be irradiated with the irradiation light during the optical measurement, thereby preventing widening of the pupil 15.

Figure 6:
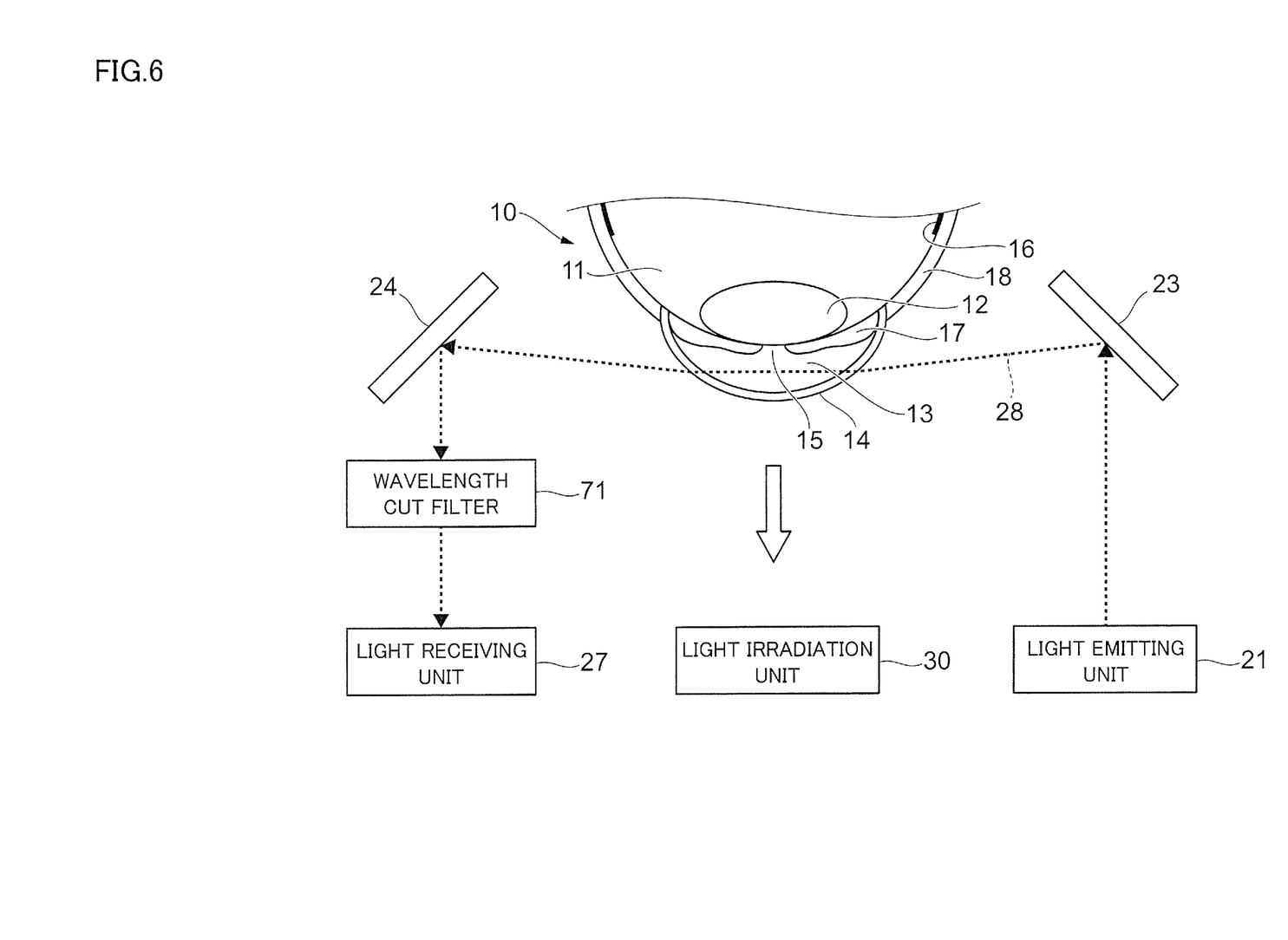
FIG. 6 illustrates an exemplary configuration of the optical measuring device according to the second exemplary embodiment.

FIG. 6 illustrates an exemplary configuration of the optical measuring device 1 according to the second exemplary embodiment. The figure schematically illustrates the optical measuring device 1 including the eyeball 10 when viewed from above. The optical measuring device 1 of the second exemplary embodiment has the same configuration as the optical measuring device 1 of the first exemplary embodiment shown in FIG. 1 except for a wavelength cut filter 71. Accordingly, FIG. 6 omits the polarizer 22, the compensator 25 and the analyzer 26 shown in FIG. 1.

The wavelength cut filter 71 prevents (blocks) the irradiation light emitted by the light irradiation unit 30 to the eyeball 10 from entering the light receiving unit 27. The wavelength cut filter 71 is arranged on the optical path 28 so that the irradiation light does not enter the light receiving unit 27.

For example, assume that the measuring light emitted by the light emitting unit 21 is infrared light and the irradiation light emitted by the light irradiation unit 30 to the eyeball 10 is blue light with a wavelength of 450 nm. In this case, the wavelength cut filter 71 may be one that prevents passage of light with a wavelength of 600 nm or less.

Even if the light irradiation unit 30 continues to irradiate the eyeball 10 with the irradiation light, which is blue light, during the optical measurement, the wavelength cut filter 71 does not allow the irradiation light to enter the light receiving unit 27. That is, the irradiation light does not affect the optical measurement.

The combination of the wavelengths of the measuring light and the irradiation light may be other than that described above, as long as the irradiation light has a wavelength of visible light.

The wavelength cut filter 71 is, for example, an interference filter that is composed of a stack of dielectric layers each having a different refractive index.

Figure 7:
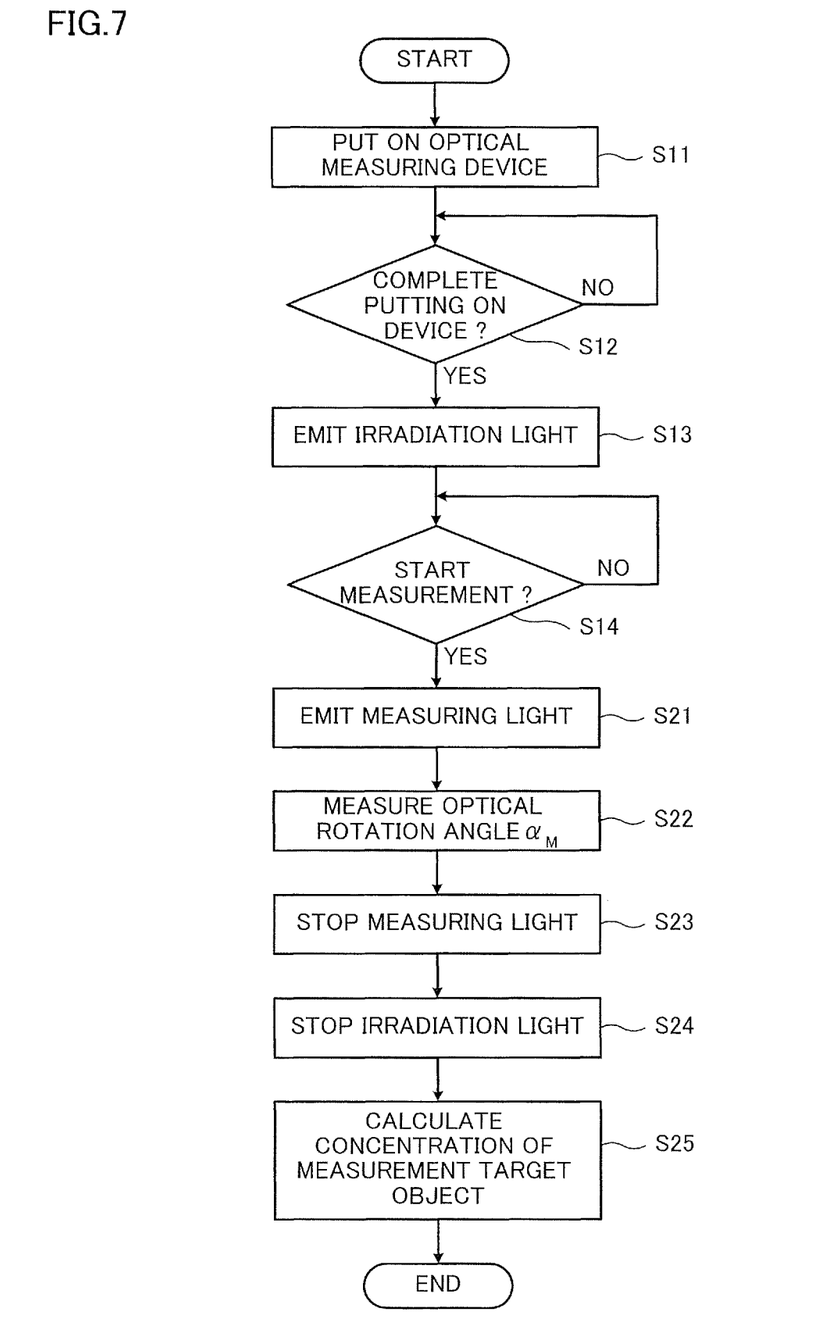
FIG. 7 is a flowchart for explaining the optical measuring method for measuring a concentration of an optically active substance contained in the aqueous humor in the anterior chamber by means of the optical measuring device according to the second exemplary embodiment.

FIG. 7 is a flowchart for explaining the optical measuring method for measuring a concentration of an optically active substance contained in the aqueous humor in the anterior chamber 13 by means of the optical measuring device 1 according to the second exemplary embodiment.

Steps 11-14 are the same as those in the flowchart of FIG. 5.

If the determination at step 14 is positive (YES), that is, if an optical measurement has been commanded, the controller 40 controls the light emitting unit 21 to emit the measuring light (step 21). The controller 40 then adjusts the optical system 20 to establish the optical path 28 that passes through the anterior chamber 13, and measures an optical rotation angle $\alpha_M$ on the basis of the measuring light that has passed through the aqueous humor in the anterior chamber 13 (step 22). Upon completion of the measurement, the controller 40 stops the light emitting unit 21 from emitting the measuring light (step 23). Then, the controller 40 stops the light irradiation unit 30 from emitting the irradiation light (step 24).

Then, the controller 40 sends optical measurement data, such as the measured optical rotation angle $\alpha_M$, to the calculation unit 60.

In response, the calculation unit 60 calculates a concentration of a target optically active substance (measurement target object) contained in the aqueous humor (step 25).

The controller 40 may then receive the data on the concentration of the measurement target object calculated by the calculation unit 60 and display the concentration on the light irradiation unit 30.

Steps 21-23 of the flowchart shown in FIG. 7 are the same as steps 16-18 of the flowchart shown in FIG. 5 of the first exemplary embodiment. Further, step 25 is the same as step 19 of the flowchart shown in FIG. 5 of the first exemplary embodiment.

Since the eyeball 10 continues to be irradiated with the irradiation light during the optical measurement, the pupil 15 is kept narrowed. In other words, the pupil 15 is kept from widening during the optical measurement. This prevents the measuring light with a high energy density from reaching the retina 16.

Third Exemplary Embodiment

In the first and the second exemplary embodiments, the pupil 15 is narrowed by the irradiation light from the light irradiation unit 30. However, the size of the pupil 15 is not measured in these exemplary embodiments.

The third exemplary embodiment calculates the size of the pupil 15 (pupil diameter D in this specific example) and determines that the pupil 15 has been narrowed to a pupil diameter D that is smaller than or equal to a predetermined value, before starting an optical measurement with the measuring light. That is, the measuring light is emitted upon confirmation that the pupil 15 has been narrowed. This prevents the measuring light with a high energy density from reaching the retina 16.

Figure 8:
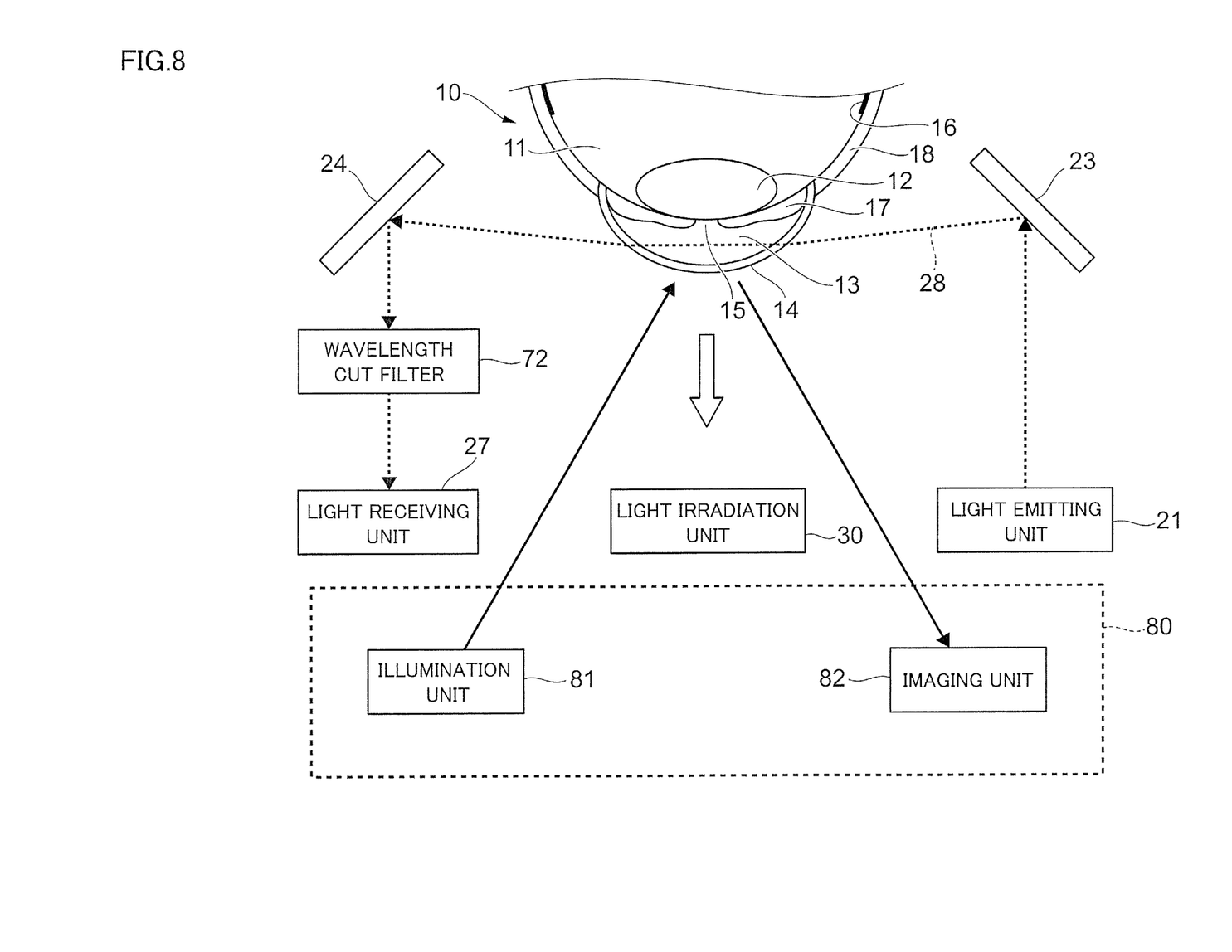
FIG. 8 illustrates an exemplary configuration of the optical measuring device according to the third exemplary embodiment.

FIG. 8 illustrates an exemplary configuration of the optical measuring device 1 according to the third exemplary embodiment. The figure schematically illustrates the optical measuring device 1 including the eyeball 10 when viewed from above. The optical measuring device 1 of the third exemplary embodiment has the same configuration as the optical measuring device 1 of the first exemplary embodiment shown in FIG. 1 except for a wavelength cut filter 72 and a pupil diameter calculation unit 80. Accordingly, FIG. 8 omits the polarizer 22, the compensator 25 and the analyzer 26 shown in FIG. 1.

The pupil diameter calculation unit 80 includes an illumination unit 81 that emits illumination light to the eyeball 10, and an imaging unit 82 that images the illumination light reflected from the eyeball 10. The pupil diameter calculation unit 80 calculates the pupil diameter D on the basis of an image of the eyeball 10 taken by the imaging unit 82. Note that this calculation of the pupil diameter D may be performed by the controller 40.

The illumination unit 81 is, for example, a lamp that emits near-infrared light to the eyeball 10.

The imaging unit 82 is, for example, a camera that has an imaging element with multiple pixels, such as a CCD imaging element and a CMOS imaging element, and takes a near-infrared image of the eyeball 10.

The pupil diameter D is calculated by, for example, counting a number of pixels of the part corresponding to the pupil 15 within the near-infrared image of the eyeball 10 taken by the imaging unit 82.

The pupil diameter calculation unit 80 has a configuration similar to a so-called eye tracking system. The pupil diameter calculation unit 80 may have other configurations, such as one without the imaging unit 82.

If the pupil diameter D of the pupil 15 calculated from the image of the pupil 15 taken by the pupil diameter calculation unit 80 is smaller than or equal to a predetermined value (pupil diameter $D_0$), the light emitting unit 21 emits the measuring light for optical measurement of the eyeball 10.

The wavelength cut filter 72 prevents the light emitted by the illumination unit 81 of the pupil diameter calculation unit 80 (e.g. near-infrared light) and the light emitted by the light irradiation unit 30 (e.g. blue light) from entering the light receiving unit 27. The wavelength cut filter 72 is composed of the wavelength cut filter 71 of the second exemplary embodiment and an additional wavelength cut filter that prevents (blocks) the passage of the light emitted by the illumination unit 81 of the pupil diameter calculation unit 80 (e.g. near-infrared light).

The wavelength cut filter 72 may be a stack of the wavelength cut filter 71 and a filter that prevents (blocks) the passage of the light emitted by the illumination unit 81 of the pupil diameter calculation unit 80 (e.g. near-infrared light). Alternatively, the wavelength cut filter 72 may be a single filter configured to block wavelengths of both the light emitted by the illumination unit 81 of the pupil diameter calculation unit 80 (e.g. near-infrared light) and the light emitted by the light irradiation unit 30 (e.g. blue light).

The wavelength cut filter 72 is arranged on the optical path 28 so that the wavelength cut filter 72 prevents (blocks) the light emitted by the illumination unit 81 of the pupil diameter calculation unit 80 (e.g. near-infrared light) and the light emitted by the light irradiation unit 30 (e.g. blue light) from entering the light receiving unit 27.

Here, the explanation is given assuming that emission of the irradiation light from the light irradiation unit 30 and the illumination light from the illumination unit 81 of the pupil diameter calculation unit 80 is continued during the optical measurement.

Note that, if emission of both of the irradiation light from the light irradiation unit 30 and the illumination light from the illumination unit 81 of the pupil diameter calculation unit 80 is stopped prior to the optical measurement as in the first exemplary embodiment, the wavelength cut filter 72 is not required.

If emission of one of the irradiation light from the light irradiation unit 30 and the illumination light from the illumination unit 81 of the pupil diameter calculation unit 80 is stopped prior to the optical measurement, the wavelength cut filter 72 may be replaced with a filter that prevents (blocks) the other light emitted during the optical measurement.

Figure 9:
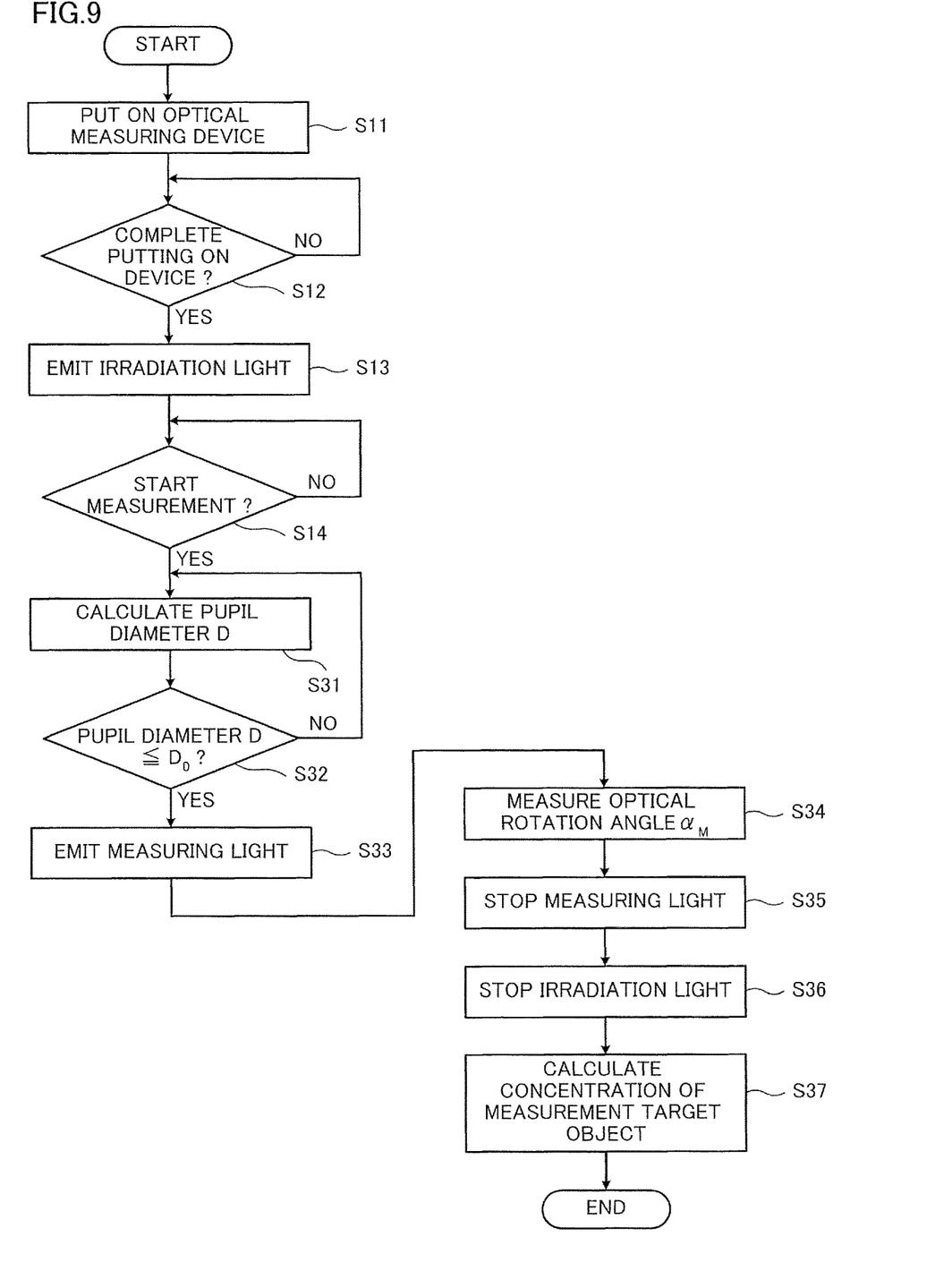
FIG. 9 is a flowchart for explaining the optical measuring method for measuring a concentration of an optically active substance contained in the aqueous humor in the anterior chamber by means of the optical measuring device according to the third exemplary embodiment.

FIG. 9 is a flowchart for explaining the optical measuring method for measuring a concentration of an optically active substance contained in the aqueous humor in the anterior chamber 13 by means of the optical measuring device 1 according to the third exemplary embodiment.

Steps 11-14 are the same as those in the flowchart of FIG. 5.

If the determination at step 14 is positive (YES), that is, if an optical measurement has been commanded, the controller 40 controls the pupil diameter calculation unit 80 to calculate the pupil diameter D of the eyeball 10 (step 31).

The controller 40 then determines whether the pupil diameter D is smaller than or equal to the predetermined pupil diameter $D_0$ (step 32).

If the determination at step 32 is negative (NO), that is, if the pupil diameter D is larger than the predetermined pupil diameter $D_0$, the process returns to step 31 and the controller 40 controls the pupil diameter calculation unit 80 to calculate the pupil diameter D of the eyeball 10.

If the determination at step 32 is positive (YES), that is, if the pupil diameter D is smaller than or equal to the predetermined pupil diameter $D_0$, the controller 40 controls the light emission unit 21 to emit the measuring light (step 33). The controller 40 then adjusts the optical system 20 to establish the optical path 28 that passes through the anterior chamber 13, and measures an optical rotation angle $\alpha_M$ on the basis of the measuring light that has passed through the aqueous humor in the anterior chamber 13 (step 34). Upon completion of the measurement, the controller 40 stops the light emitting unit 21 from emitting the measuring light (step 35). Then, the controller 40 stops the light irradiation unit 30 from emitting the irradiation light (step 36).

Then, the controller 40 sends optical measurement data, such as the measured optical rotation angle $\alpha_M$, to the calculation unit 60.

In response, the calculation unit 60 calculates a concentration of a target optically active substance (measurement target object) contained in the aqueous humor (step 37).

The controller 40 may then receive the data on the concentration of the measurement target object calculated by the calculation unit 60 and display the concentration on the light irradiation unit 30.

Steps 33-35 of the flowchart shown in FIG. 9 are the same as steps 16-18 of the flowchart shown in FIG. 5 of the first exemplary embodiment. Further, step 37 is the same as step 19 of the flowchart shown in FIG. 5 of the first exemplary embodiment.

In the above explanation, the pupil diameter D is used to evaluate the size of the pupil 15 of the eyeball 10. However, any other parameter may be used to evaluate the size of the pupil 15, such as an area of the pupil 15. In this case, the pupil diameter calculation unit 80 may be replaced with a unit for calculating such other parameter, such as a pupil area calculation unit.

In the first to the third exemplary embodiments, the light irradiation unit 30 starts emission of the irradiation light after the subject completes putting on the optical measuring device 1. To allow the subject to easily put on the optical measuring device 1, the light irradiation unit 30 may emit irradiation light with a lower luminance than the luminance used to narrow the pupil 15 when the subject puts on the optical measuring device 1.

In the first to the third exemplary embodiments, the explanation has been given of the method to calculate a concentration of a target optically active substance contained in the aqueous humor as an example. However, the optical measuring device 1 may be used for an optical measurement of any other characteristic of the aqueous humor.

Further, the optical measuring device 1 configured as above is applicable to determining a characteristic of the cornea or other parts of the eyeball 10 present on the optical path 28, instead of a characteristic of the aqueous humor. In other words, the configuration explained in the above first to the third exemplary embodiments is applicable as long as the optical measuring device 1 is used to calculate a characteristic of the eyeball 10 by emitting light to the eyeball 10 from the outside and causing the light to pass through the cornea 14 and the aqueous humor in the anterior chamber 13.

Although the above explanation has been given using the left eye, the optical measuring device 1 is applicable to an optical measurement of the right eye.

The controller 40 and the calculation unit 60 may be integrated into a single unit. Also, data transfer between the controller 40 and the calculation unit 60 may be performed either by wire or wirelessly.

Further, the first to the third exemplary embodiments are applicable to a flare cell meter that emits measuring light obliquely to the anterior chamber 13 and measures diffusion (scattering) of the light in the anterior chamber 13 based on the reflected light. Providing the light irradiation unit 30 to narrow the size of the pupil 15 enables to prevent a high-energy density light, such as a laser light, from reaching the retina 16.

The foregoing description of the present exemplary embodiments of the present invention has been provided for the purposes of illustration and description. It is not intended to be exhaustive or to limit the invention to the precise forms disclosed. Obviously, many modifications and variations will be apparent to practitioners skilled in the art. The present exemplary embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An eyeball optical measuring device comprising:
   an optical measuring unit configured to irradiate an eyeball of a subject with measuring light to perform an optical measurement of the eyeball; and
   a light irradiation unit configured to irradiate the eyeball with irradiation light for making a pupil diameter of the eyeball smaller prior to the optical measurement by the optical measuring unit, the irradiation light having a lower energy density than an energy density of the measuring light,
   wherein the measuring light travels along an optical path in a direction intersecting another direction toward the fundus of the eyeball, the direction passing across an anterior chamber of the eyeball.

2. The eyeball optical measuring device according to claim 1, wherein the light irradiation unit irradiates the eyeball with the irradiation light at a timing that is prior to the optical measurement by the optical measuring unit and that ensures that a size of a pupil of the eyeball narrowed by the irradiation light does not return to a pre-irradiation size during the optical measurement.

3. The eyeball optical measuring device according to claim 1, further comprising a pupil diameter calculation unit configured to calculate a pupil diameter of the eyeball, wherein
   the optical measuring unit configured to perform the optical measurement of the eyeball if the pupil diameter calculated by the pupil diameter calculation unit becomes smaller than or equal to a predetermined value by being irradiated with the irradiation light from the light irradiation unit.

4. The eyeball optical measuring device according to claim 1, wherein the light irradiation unit irradiates the eyeball with the irradiation light during the optical measurement by the optical measuring unit.

5. The eyeball optical measuring device according to claim 1, wherein wavelengths of the measuring light and the irradiation light are different from each other.

6. The eyeball optical measuring device according to claim 5, wherein the optical measuring unit includes a wavelength cut filter that prevents the irradiation light from entering a light receiving unit for receiving the measuring light.

7. An eyeball optical measuring method for optically measuring an eyeball of a subject, comprising:
   irradiating the eyeball with irradiation light that has a lower energy density than an energy density of measuring light used for the optical measurement; and
   irradiating the eyeball with the measuring light to optically measure the eyeball,
   wherein the measuring light travels along an optical path in a direction intersecting another direction toward the fundus of the eyeball, the direction passing across an anterior chamber of the eyeball.

8. The eyeball optical measuring method according to claim 7, further comprising:
   calculating a pupil diameter of the eyeball,
   wherein the eyeball is optically measured in response to the pupil diameter calculated becoming smaller than or equal to a predetermined value after being irradiated with the irradiation light.

9. The eyeball optical measuring device according to claim 1, wherein the measuring light is directed into the eyeball at an angle different than the irradiation light.

10. The eyeball optical measuring method according to claim 7, wherein the measuring light is directed into the eyeball at an angle different than the irradiation light.

11. The eyeball optical measuring device according to claim 1, wherein the optical measuring unit configured to irradiates the measuring light to measure an optical rotation angle.

12. The eyeball optical measuring method according to claim 7, wherein the measuring light is irradiated in a manner to measure an optical rotation angle.

13. The eyeball optical measuring device according to claim 1,
    wherein the irradiation unit is a liquid crystal display.
14. The eyeball optical measuring device according to claim 13,
    wherein the liquid crystal display is configured to display a mark to guide the direction of the eyeball.
15. The eyeball optical measuring device according to claim 1,
    wherein the irradiation unit is a LED.
16. The eyeball optical measuring device according to claim 1, wherein the measuring light travels along an optical path that passes across an anterior chamber of the eyeball from one of an internal canthus side of the anterior chamber and an external canthus side of the anterior chamber toward the other of the internal canthus side and the external canthus side.

* * * * *